US010809186B2

(12) United States Patent
Mefford et al.

(10) Patent No.: US 10,809,186 B2
(45) Date of Patent: Oct. 20, 2020

(54) OPTICAL DETECTION SYSTEM AND METHOD (71) Applicant: The Boeing Company, Chicago, IL (US)

(72) Inventors: David K. Mefford, Huntsville, AL (US); Robert A. Smith, Huntsville, AL (US); John R. Lowell, Fairfax, VA (US)

(73) Assignee: THE BOEING COMPANY, Chicago, IL (US)

( * ) Notice: Subject to any disclaimer, the term of this patent is extended or adjusted under 35 U.S.C. 154(b) by 25 days.

(21) Appl. No.: 16/220,485

(22) Filed: Dec. 14, 2018

(65) Prior Publication Data
US 2020/0191708 A1 Jun. 18, 2020

(51) Int. Cl.
G01N 21/3504 (2014.01)
G01N 33/00 (2006.01)
G01J 3/45 (2006.01)

(52) U.S. Cl.
CPC ............ G01N 21/3504 (2013.01); G01J 3/45 (2013.01); G01N 33/004 (2013.01)

(58) Field of Classification Search
CPC ...... G01N 21/3504; G01N 33/004; G01J 3/45
See application file for complete search history.

(56) References Cited

U.S. PATENT DOCUMENTS 6,353,476 B1 * 3/2002 Allen .................. G01J 3/44
356/301
6,985,818 B1 1/2006 Samuels
2007/0153269 A1 * 7/2007 Wang .................. G08B 21/12
356/301
2013/0265568 A1 10/2013 Micheels et al.
2015/0323450 A1 * 11/2015 Lipson .............. H01L 31/02327
356/437

FOREIGN PATENT DOCUMENTS

EP 2219022 A1 8/2020
WO 2018/213212 A1 11/2018

OTHER PUBLICATIONS

Extended European Search Report dated Apr. 21, 2020 in corresponding European Application No. 19216248.5, 9 pages.

* cited by examiner

Primary Examiner — David P Porta
Assistant Examiner — Meenakshi S Sahu
(74) Attorney, Agent, or Firm — MH2 Technology Law Group LLP (57) ABSTRACT An optical detection method and device are provided. The optical detection method includes directing an optical beam toward a target; selecting a first test sensor from among a plurality of test sensors to compare with radiation received from the target, wherein the first test sensor comprises a first test chemical; receiving a reflected or scattered optical beam from the target; comparing a first spectrum from the first test chemical with a spectrum of the reflected or scattered optical beam that was received using a linear detector array; determining a likely chemical from the target based on the comparing using a hardware processor; and providing an output based on the determining.

16 Claims, 6 Drawing Sheets

Selecting a second test sensor from among a plurality of test sensors to compare with radiation received from the target, wherein the second test sensor comprises a second test chemical

404

Comparing a second spectrum from the second test chemical with the spectrum of the reflected or scattered optical beam that was received using the linear detector array

406

Determining whether the likely chemical from the target is closer to the first spectrum or the second spectrum using the hardware processor

OPTICAL DETECTION SYSTEM AND METHOD

FIELD OF THE DISCLOSURE

The present disclosure is directed to systems and methods for chemical detection. More particularly, the present disclosure is directed to remote chemical detection systems and methods using optical absorption detection with a matched reference.

BACKGROUND

It is known in the art to detect certain constituents in a chemical cloud in the air by spectral analysis of the molecules making up the cloud. This type of chemical detection has many applications, including detecting natural gas leaks from underground pipes, chemical clouds from chemical spills, volatile organic vapor (VOC) from chemical processes, pollution from smoke stacks and the like, military chemical warfare agents, and other toxic gases present in the air. Typically, this type of spectral analysis of a chemical cloud is performed remotely, sometimes up to 10-20 km away, because the constituents in the cloud may be toxic, and thus a threat to health, or it may not be possible to directly detect the chemical cloud. The distance the detecting instrument has to be from the cloud for this remote type of passive sensing depends on the particular application, and different systems exist for different applications.

To perform this type of detection and analysis, a spectrometer, such as a Fourier transform infrared (FTIR) spectrometer, is directed towards the chemical agent cloud from a remote location, so that it passively receives emissions therefrom. Typical optical absorption detection systems operate independent of each other and rely on long optical path lengths to absorb enough of a species for detection. The spectral display generated by the spectrometer from the emissions provides emission lines and bands at certain wavelengths that is indicative of the atoms and molecules in the cloud. Because each material has its own spectral "fingerprint" representative of its molecules, the detected spectral display can be compared to a known "fingerprint" of a particular chemical to determine if that chemical exists in the cloud.

What is needed is an improved remote chemical detection system that addresses various problem of the conventional approaches.

SUMMARY

In accordance with examples of the present disclosure, an optical detection method is provided that comprises directing an optical beam toward a target; selecting a first test sensor from among a plurality of test sensors to compare with radiation received from the target, wherein the first test sensor comprises a first test chemical; receiving a reflected or scattered optical beam from the target; comparing a first spectrum from the first test chemical with a spectrum of the reflected or scattered optical beam that was received using a linear detector array; determining a likely chemical from the target based on the comparing using a hardware processor; and providing an output based on the determining.

In some examples, the optical detection method further comprises selecting a second test sensor from among a plurality of test sensors to compare with radiation received from the target, wherein the second test sensor comprises a second test chemical; comparing a second spectrum from the second test chemical with the spectrum of the reflected or scattered optical beam that was received using the linear detector array; and determining whether the likely chemical from the target is closer to the first spectrum or the second spectrum using the hardware processor.

In some examples, each of the plurality of test sensors comprise a nanomaterial that is impregnated with a different test chemical. In some examples, the directing further comprises expanding the optical beam with a beam expander and steering the optical beam with a beam steering mirror, wherein the optical beam at the target comprises a plurality of spatially displaced optical beams. In some examples, the selecting further comprises heating the first test sensor to a temperature sufficient to release the first test chemical from the first test sensor. In some examples, the first test sensor is selected based on an initial assessment of the likely chemical from the target. In some examples, each test sensor of the plurality of test sensors is tested prior to providing the output.

In accordance with examples of the present disclosure, an optical detection device is provide. The optical detection device comprises a transmitter configured to direct an optical beam toward a target and configured to select a first test sensor from among a plurality of test sensors to compare with radiation received from the target, wherein the first test sensor comprises a first test chemical; a receiver configured to receive a reflected or scattered optical beam from the target; a linear detector array configured to compare a first spectrum from the first test chemical with a spectrum of the reflected or scattered optical beam that was received; a hardware processor configured to determine a likely chemical from the target based on the comparing; and an output interface configured to provide an output based on the determining. In some examples, each of the plurality of test sensors comprise a nanomaterial that is impregnated with a different test chemical. In some examples, each of the plurality of test sensors comprise a capsule with a different test chemical. In some examples, the transmitter further comprises a heat source configured to heat the first test sensor to a temperature sufficient to release the first test chemical from the first test sensor. In some examples, the transmitter further comprises a beam expander configured to expand the optical beam and a beam steering mirror configured to steer the optical beam, wherein the optical beam at the target comprises a plurality of spatially displaced optical beams. In some examples, the optical detection device further comprises an integrated near infrared comb device, an integrated mid-infrared comb device, or both, where an output of the integrated near infrared comb device and the integrated mid-infrared comb device is provided to the transmitter. In some examples, the receiver further comprises a beam focusing device configured to receive the reflected or scattered optical beam from the target and one or more scan mirrors configured to provide one or more scanned optical beam to the linear detector array. In some examples, the first test sensor is selected based on an initial assessment of the likely chemical from the target. In some examples, each test sensor of the plurality of test sensors is tested prior to providing the output.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrate aspects of the present teachings and together with the description, serve to explain the principles of the present teachings.

It should be noted that some details of the figures have been simplified and are drawn to facilitate understanding rather than to maintain strict structural accuracy, detail, and scale.

DESCRIPTION

Reference will now be made in detail to the present teachings, examples of which are illustrated in the accompanying drawings. In the drawings, like reference numerals have been used throughout to designate identical elements. In the following description, reference is made to the accompanying drawings that form a part thereof, and in which is shown by way of illustration specific examples of practicing the present teachings. The following description is, therefore, merely exemplary.

Generally speaking, aspects of the present disclosure provides for an optical detection system and method that using a matched absorption filter that provide the ability to "pull" a chemical at a target location out of the background and compare a spectrum of the chemical to with spectrums from one or more test chemicals. The optical detection of a low concentration compound mixed with background via absorption is enhanced by optically combining a matched optical absorption feature without background. The matched feature is determined by a detection system and also serves as the source for releasing the matched absorption feature. The optical detection system and method provides for (1) the use of a matched chemical absorption feature optical combined with a signature in background, (2) the use of an orthogonal sensor to determine the chemical release, and (3) the use of the same orthogonal sensor type to generate the release of suspect chemical for optical absorption detection. The optical detection system and method provides for an enhancement to in matching gaseous outputs of chemicals, including but are not limited to TNT.

The optical detection system and method can use nanotube chemical sensors that can be heated to release a chemical bonded to the nanotube so that an optical beam probes the released chemical. The optical detection system and method probes the environment and uses subtractive detection to determine a likely chemical in the environment. The nanotube can include a functionalized surface with chemical bonds that, when heated, the chemical is released. The optical beam is directed through the released gas and is analyzed to determine if the environment has the chemical. The optical detection system and method can use optical spectroscopy of the chemicals through either absorption or emission spectroscopy. The optical detection system and method can be used for any type of environmental monitoring, explosives detection, environmental issues at smokestacks, pollution monitors, fire detection.

Figure 1:
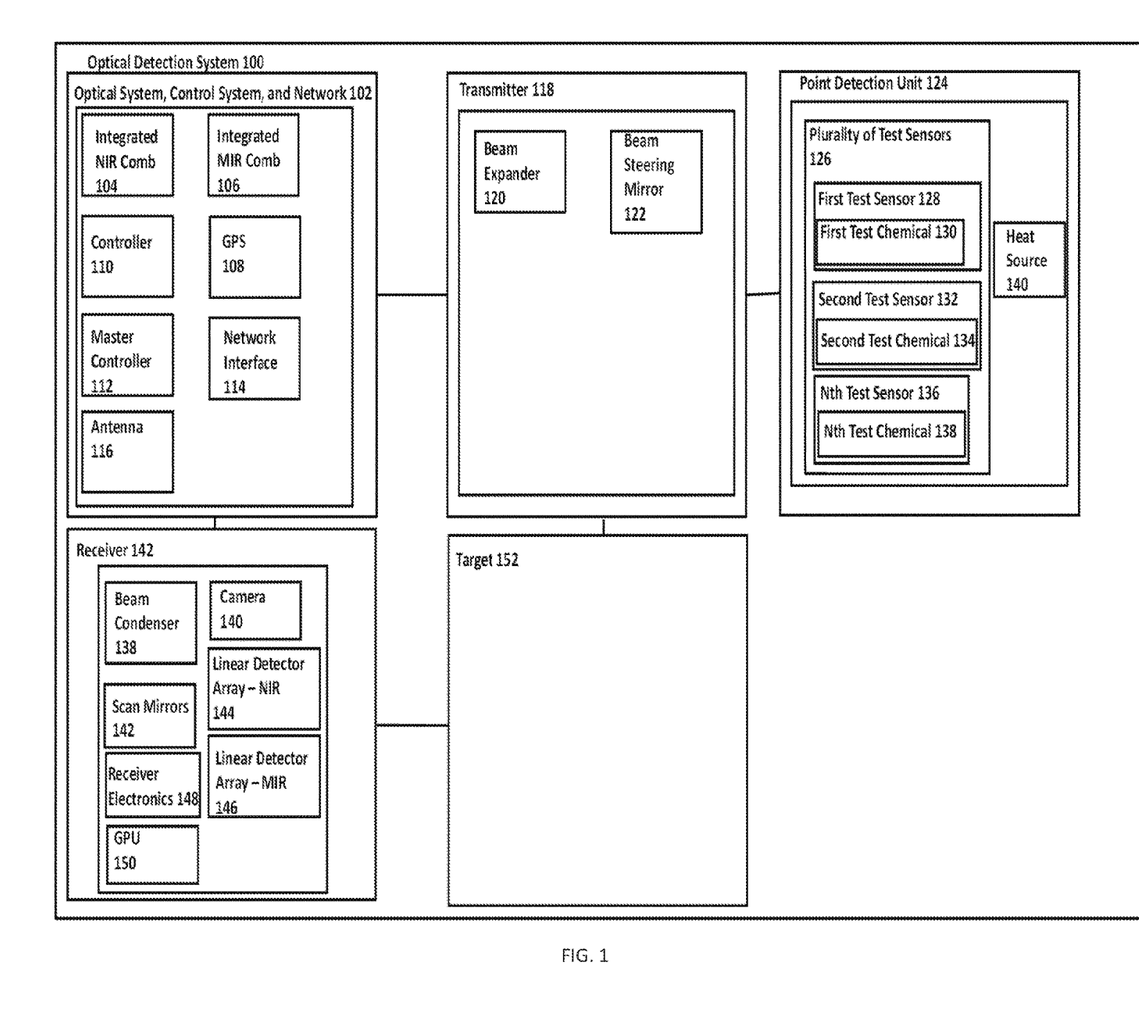
FIG. 1 illustrates a block diagram of an optical detection system for chemical detection using a matched reference, according to an implementation.

FIG. 1 illustrates a block diagram of an optical detection system 100 for chemical detection using a matched reference, according to an implementation. Optical detection system 100 comprises optical system, control system, and network 102 elements that are configured to produce and control an optical beam. The optical system of optical detection system 100 can include one or more of integrated near infrared ("NIR") frequency comb 104 laser system and integrated mid infrared ("MIR") frequency comb 106 laser system. The frequency comb laser system is a laser source whose spectrum is made up of a series of discrete, equally spaced frequency lines. The frequency comb laser can be generated by a number of mechanisms, including periodic modulation (in amplitude and phase) of a continuous-wave laser, four wave mixing in nonlinear media or stabilization of a pulse train generated by a mode-locked laser. In one non-limiting example, the laser used for frequency-comb generation can be Ti:sapphire solid-state lasers or Er:fiber lasers with repetition rates typically between 100 MHz and 1 GHz or even going as high as 10 GHz.

Optical system, control system, and network 102 elements also include controller 110 that is configured to control the operation of integrated NIR frequency comb 104 and integrated MIR frequency comb 106. Optical system, control system, and network 102 also includes network interface 114 and antenna 116. Global positioning system ("GPS") module 108 can be in communication with controller 110 and master controller 112. Optical system, control system, and network 102 elements also comprises an output interface that is configured to provide an output for a user and/or to be provided to computer system over a network by network interface 114 and antenna 116.

Optical detection system 100 also comprises transmitter 118. Transmitter 118 is configured to direct an optical beam from NIR frequency comb 104 laser system and/or MIR frequency comb 106 laser system towards target 152. Transmitter 118 can comprise beam expander 120 that is configured to expand the optical beam and beam steering mirror 122 that is configured to steer the optical beam. The optical beam at target 118 can comprise plurality of spatially displaced optical beams.

Optical detection system 100 also comprises point detection unit 124 that is configured to select a test sensor from among a plurality of test sensors 126 that is used to compare with radiation received from target 152. Plurality of test sensors 126 includes first test sensor 128, second test sensor 130, . . . , nth test sensor 132. First test sensor 128 comprises first test chemical 130, second test sensor 132 comprises second test chemical 134, and nth test sensor 136 comprises nth test chemical 138. Each of plurality of test sensors 126 comprises a nanomaterial that is impregnated with a different test chemical. Each of the plurality of test sensors 126 can comprise a capsule with a different test chemical. Point detection unit 124 can also include heat source 134 configured to heat one or more of the plurality of test sensors 126 to a temperature sufficient to release the respective test chemicals from the test sensors. In one non-limiting example, a single walled carbon nanotube material could be functionalized as mimicking a natural receptor for molecular recognition for detection of hydrogen sulfide or sulfur mustard or any number of other chemical agents with sensitivity levels of 10 ppm or less.

Receiver 142 is configured to receive a reflected or scattered optical beam from target 152. Receiver 106 comprises beam condenser 130 and camera 140 that are configured to operate in reverse to beam expander 120 by focusing the plurality of scattered and/or reflected optical beams from target 152. Receiver 106 also comprises linear detector array—NIR 144 and/or linear detector array—MIR 146, whose outputs are received by receiver electronics 148 and processed by a processor, such as by a central processing unit ("CPU") or graphics processor unit ("GPU") 150. Linear detector array—NIR 144 and/or linear detector array—MIR 146 is configured to compare one or more spectrums from one or more test chemicals, such as a first spectrum from the first test chemical, with a spectrum of the reflected or scattered optical beam that was received from target 152. The processor, such as GPU 150, is configured to determine a likely chemical from target 152 based on the results of the processor.

Figure 2:
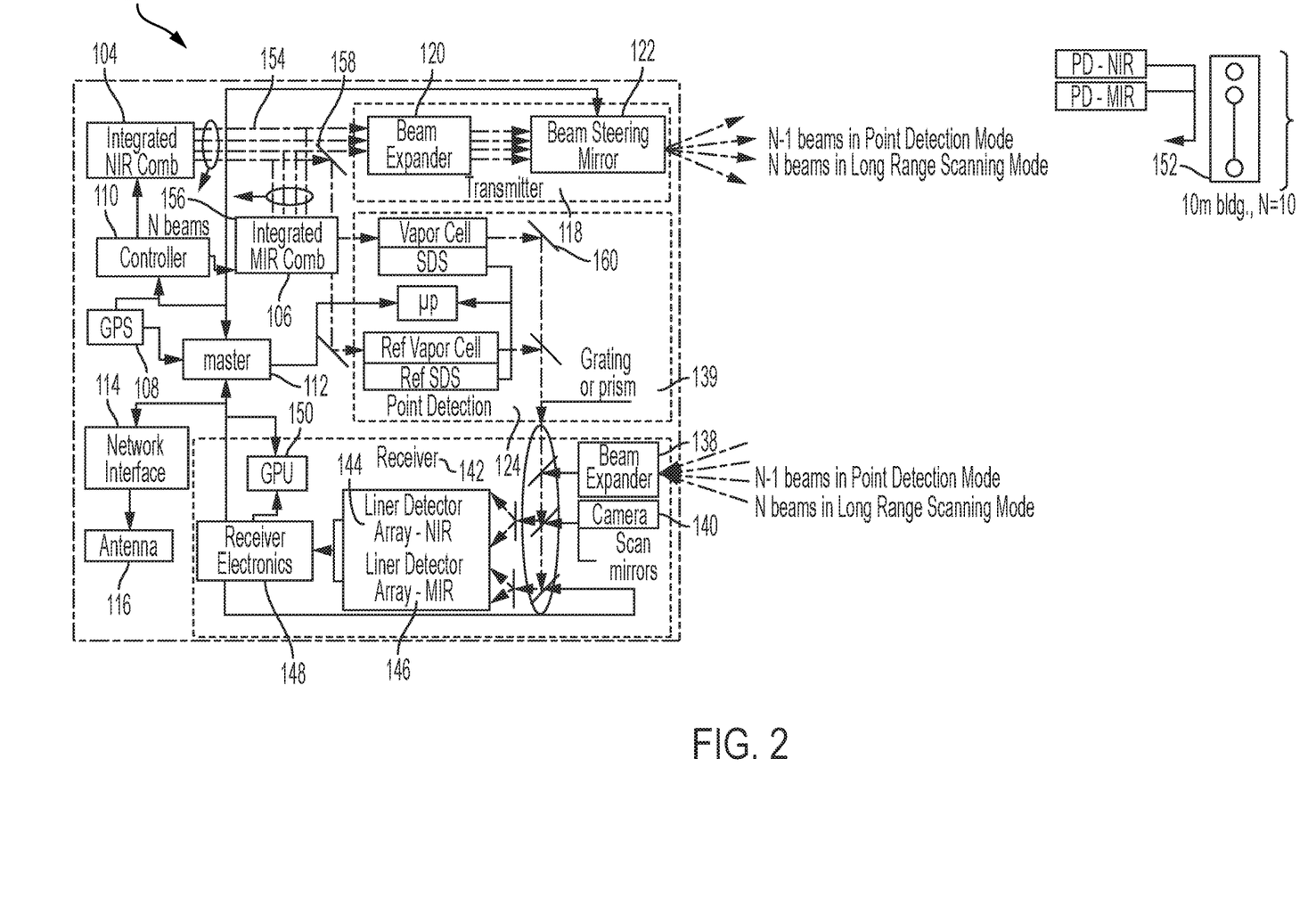
FIG. 2 illustrates a schematic view of the block diagram of FIG. 1.

FIG. 2 illustrates schematic view 200 of optical detection system 100, showing additional details. Integrated NIR frequency comb 104 and integrated MIR frequency comb 106 are configured to produce first plurality of spatially displayed optical beams 154 and second plurality of spatially displayed optical beams 156, respectively. A portion of first plurality of spatially displayed optical beams 154 and second plurality of spatially displayed optical beams 156 is directed to point detection unit 124 by first mirror 158. Radiation from point detection unit 124 is directed to receiver 142 by second mirror 160, which is combined with radiation received from target 152 by beam splitter 162 and/or grating or prism 139 to be analyzed by linear detector array—NIR 144 and/or linear detector array—MIR 146, receiver electronics 148, and GPU 150.

Figure 3:
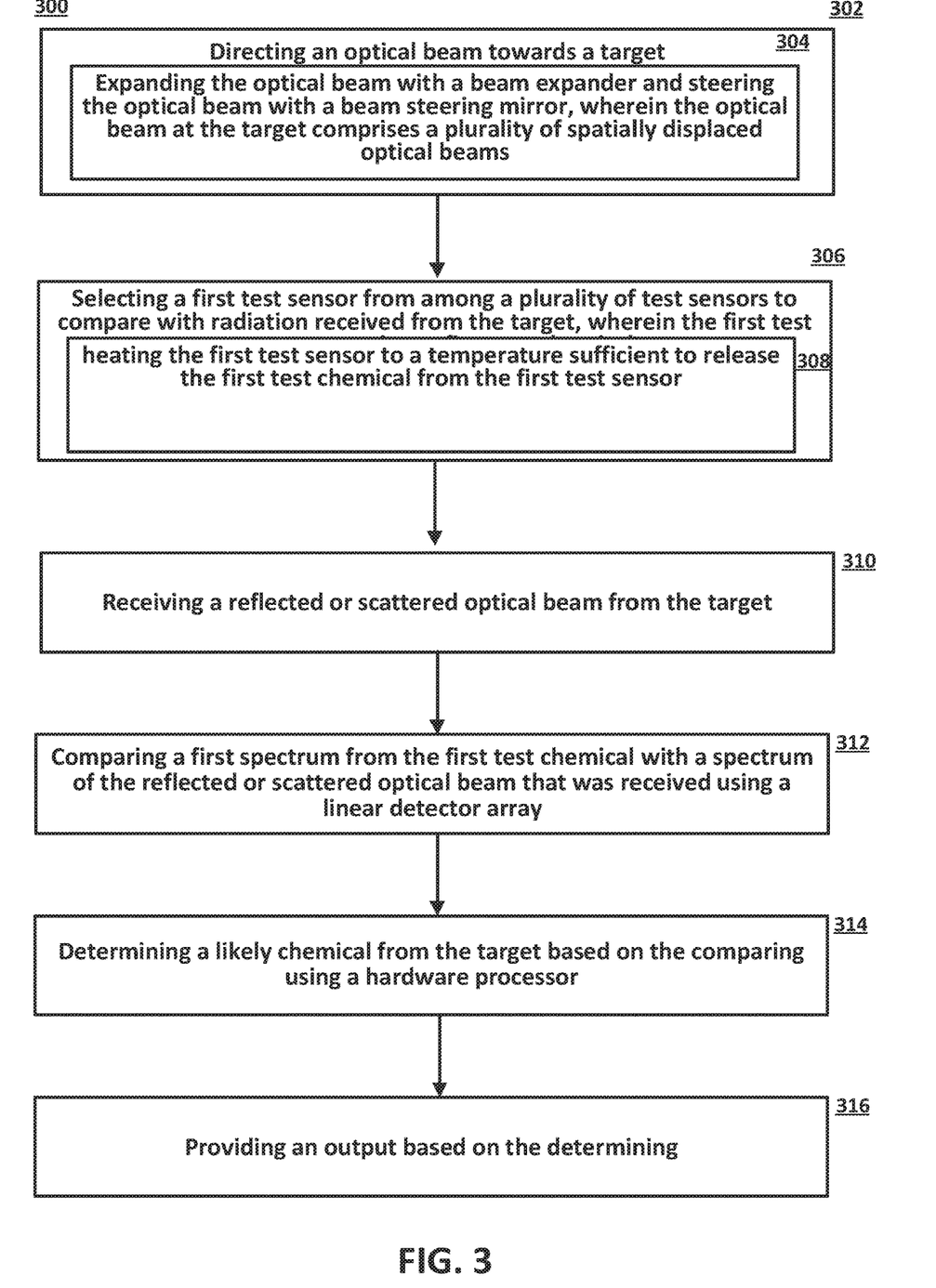
FIG. 3 shows an optical detection method 300, according to an implementation.

FIG. 3 shows an optical detection method 300, according to examples of the present disclosure. The optical detection method 300 can begin by directing, at 302, an optical beam toward target 152. In some examples, the directing further comprises expanding, at 304, the optical beam with beam expander 120 and steering the optical beam with beam steering mirror 122. The optical beam at target 152 comprises a plurality of spatially displaced optical beams.

The optical detection method 300 can continue by selecting, at 306, first test sensor 128 from among plurality of test sensors 126 to compare with radiation received from target 152. In some examples, the selecting can further comprises heating, at 308, first test sensor 128 to a temperature sufficient to release first test chemical 130 from first test sensor 128. First test sensor 128 can comprise first test chemical 130, second sensor 132 can comprises second test chemical 134, . . . , nth test sensor 136 can comprise nth test chemical 138. Each of the plurality of test sensors 126 can comprise a nanomaterial that is impregnated with a different test chemical.

The optical detection method 300 can continue by receiving, at 310, a reflected or scattered optical beam from target 152. The optical detection method 300 can continue by comparing, at 312, a first spectrum from first test chemical 130 with a spectrum of the reflected or scattered optical beam that was received using linear detector array 144, 146. For example, the local atmosphere can be interrogated by transmitter 118. The test sensor, such as first test sensor 128, is heated and first test chemical 130 is released. The local atmosphere ingested by the test sensor, such as first test sensor 128, can be interrogated by the portion of the optical beam separated by first mirror 158 from transmitter 118. The optical detection method 300 can continue by determining, at 314, a likely chemical from target 152 based on the comparing using a hardware processor. The optical detection method 300 can continue by providing, at 316, an output based on the determining. Typically a chemical spectrum is defined by its absorption features as a function of frequency. A chemical spectrum will have specific features associated with the constituents that make up the chemical compound. By identifying those specific features, a database is generated in a controlled environment with the optical detection system 100. If a background or the confluence of chemical mask or override the specific features, then a method of increasing the chemical's features is required. The addition of the matched filter's spectrum is applied, then the spectrum in question will increase in signal to background ratio. A processing method will be used to correlate the captured spectrum's signature to that stored in a database where a declaration with the highest confidence will be made.

Figure 4:
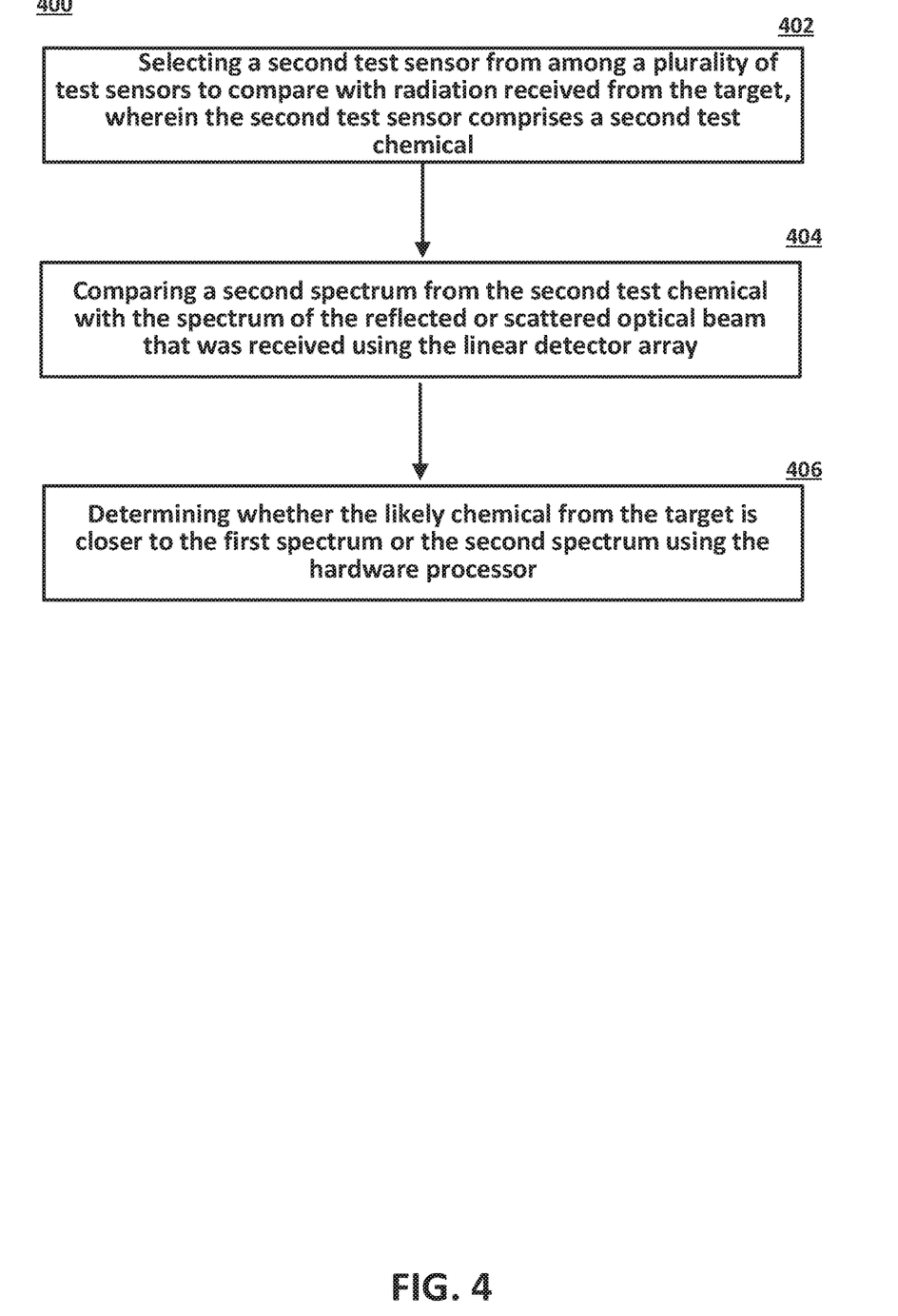
FIG. 4 shows an optical detection method 400, according to an implementation.

FIG. 4 shows the optical detection method 400, according to examples of the present disclosure. The method 400 is a continuation of the method 300. The method 400 begins by selecting, at 402, a second test sensor from among plurality of test sensors 126 to compare with radiation received from target 152. Second test sensor 132 can comprise second test chemical 134. The method 400 continues by comparing, 404, a second spectrum from second test chemical 134 with the spectrum of the reflected or scattered optical beam that was received using linear detector array 144, 146. The method 400 continues by determining, at 406, whether the likely chemical from the target is closer to the first spectrum or the second spectrum using the hardware processor.

Figure 5:
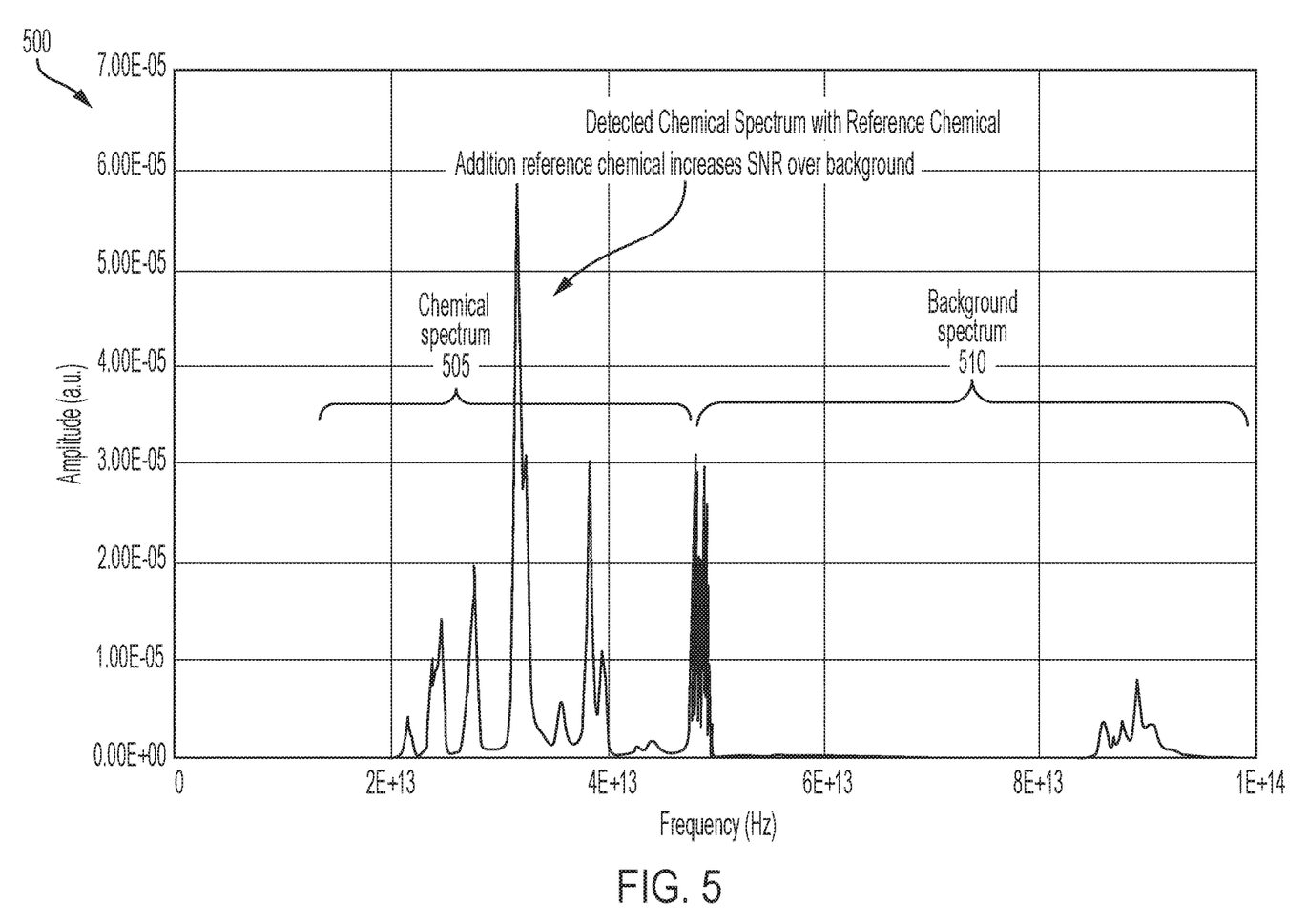
FIG. 5 shows an example spectrum 500 that can be produced by optical detection method 300, according to examples of the present disclosure.

FIG. 5 shows an example spectrum 500 that can be produced by optical detection method 300, according to examples of the present disclosure. The spectrum 500 shows a first portion 505 of a chemical spectrum with the additional of a reference chemical, such as by first test chemical 130 or second test chemical 134, which provides an increase signal-to-noise ratio over the background. The spectrum 500 also shows a second portion 510 comprising the background spectrum.

Figure 6:
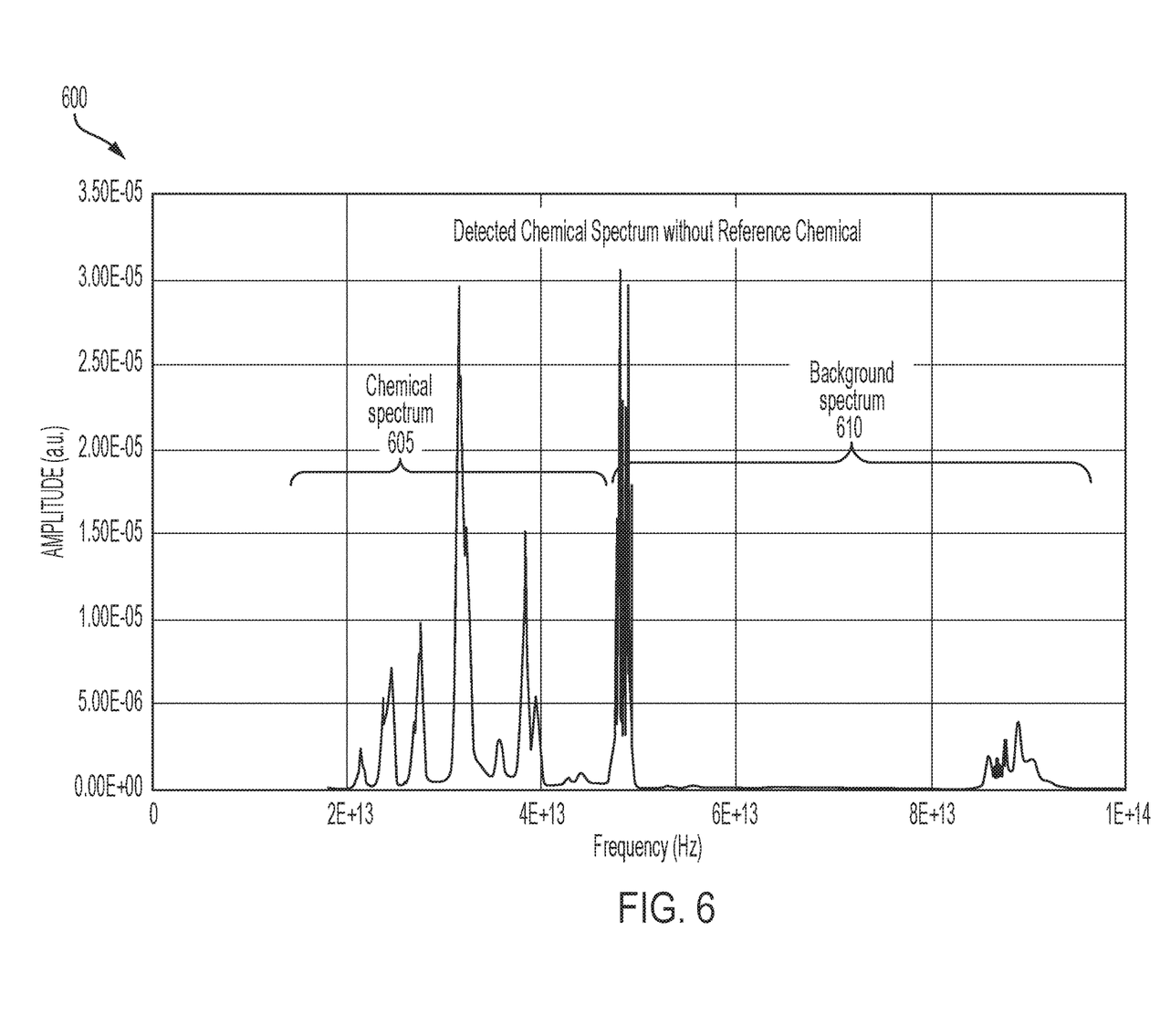
FIG. 6 shows an example spectrum 600 that does not include a reference chemical.

By comparison, FIG. 6 shows an example spectrum 600 that does not include a reference chemical. The spectrum 600 shows a first portion 605 of a chemical spectrum and a second portion 610 comprising the background spectrum.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. As used herein, the term "at least one of A and B" with respect to a listing of items such as, for example, A and B, means A alone, B alone, or A and B. Those skilled in the art will recognize that these and other variations are possible. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the intended purpose described herein. Finally, "exemplary" indicates the description is used as an example, rather than implying that it is an ideal.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompasses by the following claims.

What is claimed is:

1. An optical detection method comprising:
   directing an optical beam toward a target;
   selecting a first test sensor from among a plurality of test sensors to compare with radiation received from the target, wherein the first test sensor comprises a first nanomaterial that is impregnated with a first test chemical;
   receiving a reflected or scattered optical beam from the target;
   comparing a first spectrum from the first test chemical with a spectrum of the reflected or scattered optical beam that was received using a linear detector array;
   determining a likely chemical from the target based on the comparing using a hardware processor; and
   providing an output based on the determining.

2. The optical detection method of claim 1, further comprising:
   selecting a second test sensor from among a plurality of test sensors to compare with radiation received from the target, wherein the second test sensor comprises a second test chemical;
   comparing a second spectrum from the second test chemical with the spectrum of the reflected or scattered optical beam that was received using the linear detector array; and
   determining whether the likely chemical from the target is closer to the first spectrum or the second spectrum using the hardware processor.

3. The optical detection method of claim 1, wherein each of the plurality of test sensors comprise a nanomaterial that is impregnated with a different test chemical.

4. The optical detection method of claim 1, wherein the directing further comprises expanding the optical beam with a beam expander and steering the optical beam with a beam steering mirror, wherein the optical beam at the target comprises a plurality of spatially displaced optical beams.

5. The optical detection method of claim 1, wherein the selecting further comprises heating the first test sensor to a temperature sufficient to release the first test chemical from the first test sensor.

6. The optical detection method of claim 1, wherein the first test sensor is selected based on an initial assessment of the likely chemical from the target.

7. The optical detection method of claim 1, wherein each test sensor of the plurality of test sensors is tested prior to providing the output.

8. An optical detection device comprising:
   a transmitter configured to direct an optical beam toward a target and configured to select a first test sensor from among a plurality of test sensors to compare with radiation received from the target, wherein the first test sensor comprises a first nanomaterial that is impregnated with a first test chemical;
   a receiver configured to receive a reflected or scattered optical beam from the target;
   a linear detector array configured to compare a first spectrum from the first test chemical with a spectrum of the reflected or scattered optical beam that was received;
   a hardware processor configured to determine a likely chemical from the target based on the comparing; and
   an output interface configured to provide an output based on the determining.

9. The optical detection device of claim 8, wherein each of the plurality of test sensors comprise a nanomaterial that is impregnated with a different test chemical.

10. The optical detection device of claim 8, wherein each of the plurality of test sensors comprise a capsule with a different test chemical.

11. The optical detection device of claim 8, wherein the transmitter further comprises a heat source configured to heat the first test sensor to a temperature sufficient to release the first test chemical from the first test sensor.

12. The optical detection device of claim 8, wherein the transmitter further comprises a beam expander configured to expand the optical beam and a beam steering mirror configured to steer the optical beam, wherein the optical beam at the target comprises a plurality of spatially displaced optical beams.

13. The optical detection device of claim 8, further comprising an integrated near infrared comb device, an integrated mid-infrared comb device, or both, where an output of the integrated near infrared comb device and the integrated mid-infrared comb device is provided to the transmitter.

14. The optical detection device of claim 8, wherein the receiver further comprises a beam focusing device configured to receive the reflected or scattered optical beam from the target and one or more scan mirrors configured to provide one or more scanned optical beam to the linear detector array.

15. The optical detection device of claim 8, wherein the first test sensor is selected based on an initial assessment of the likely chemical from the target.

16. The optical detection device of claim 8, wherein each test sensor of the plurality of test sensors is tested prior to providing the output.

* * * * *